United States Patent

Knapp et al.

Patent Number: 5,300,120
Date of Patent: Apr. 5, 1994

[54] IMPLANT WITH ELECTRICAL TRANSPONDER MARKER

[75] Inventors: Terry R. Knapp, Redding, Calif.; Thomas L. Monsees, St. Louis, Mo.; Winston A. Andrews, Danville, Calif.

[73] Assignee: LipoMatrix Incorporated, Palo Alto, Calif.

[21] Appl. No.: 934,785

[22] Filed: Aug. 24, 1992

[51] Int. Cl.⁵ .................. A61F 2/02; A61F 2/28; A61F 2/30
[52] U.S. Cl. ........................... 623/11; 623/8; 623/18; 623/16
[58] Field of Search ............ 623/8, 7, 11, 18, 16; 128/419 PG

[56] References Cited

U.S. PATENT DOCUMENTS

| | | |
|---|---|---|
| 4,262,632 | 4/1981 | Hanton et al. |
| 4,361,153 | 11/1982 | Slocum et al. |
| 4,618,861 | 10/1986 | Gettens et al. |
| 4,703,756 | 11/1987 | Gough et al. |
| 4,730,188 | 3/1988 | Milheiser. |
| 4,746,830 | 5/1988 | Holland. |
| 4,854,328 | 8/1989 | Pollack. |
| 4,863,470 | 9/1989 | Carter ........................ 623/8 |
| 4,875,483 | 10/1989 | Vollmann et al. ........... 128/419 PG |
| 4,992,794 | 2/1991 | Brouwers. |
| 5,028,918 | 7/1991 | Giles et al. |
| 5,041,826 | 8/1991 | Milheiser. |
| 5,084,699 | 1/1992 | DeMichele .................. 340/825.54 |
| 5,095,309 | 3/1992 | Troyk et al. |

Primary Examiner—David Isabella
Assistant Examiner—Debra S. Brittingham
Attorney, Agent, or Firm—Rogers, Howell & Haferkamp

[57] ABSTRACT

A passive transponder may be encoded with a number or code of up to 64 binary bits and then mounted to virtually any prosthesis implanted in a human, such as a breast implant. After implantation, the transponder's code may be conveniently read with a hand held electromagnetic reader which may merely be brought within proximity of the transponder. The encoded transponder may thus be read in a non-invasive procedure and without the use of any sophisticated or potentially harmful medical equipment or technology such as X-ray. The information encoded in the transponder may correspond to patient demographics and implant data to aid in tracking the implant's manufacturer and use for medical as well as legal reasons.

27 Claims, 3 Drawing Sheets

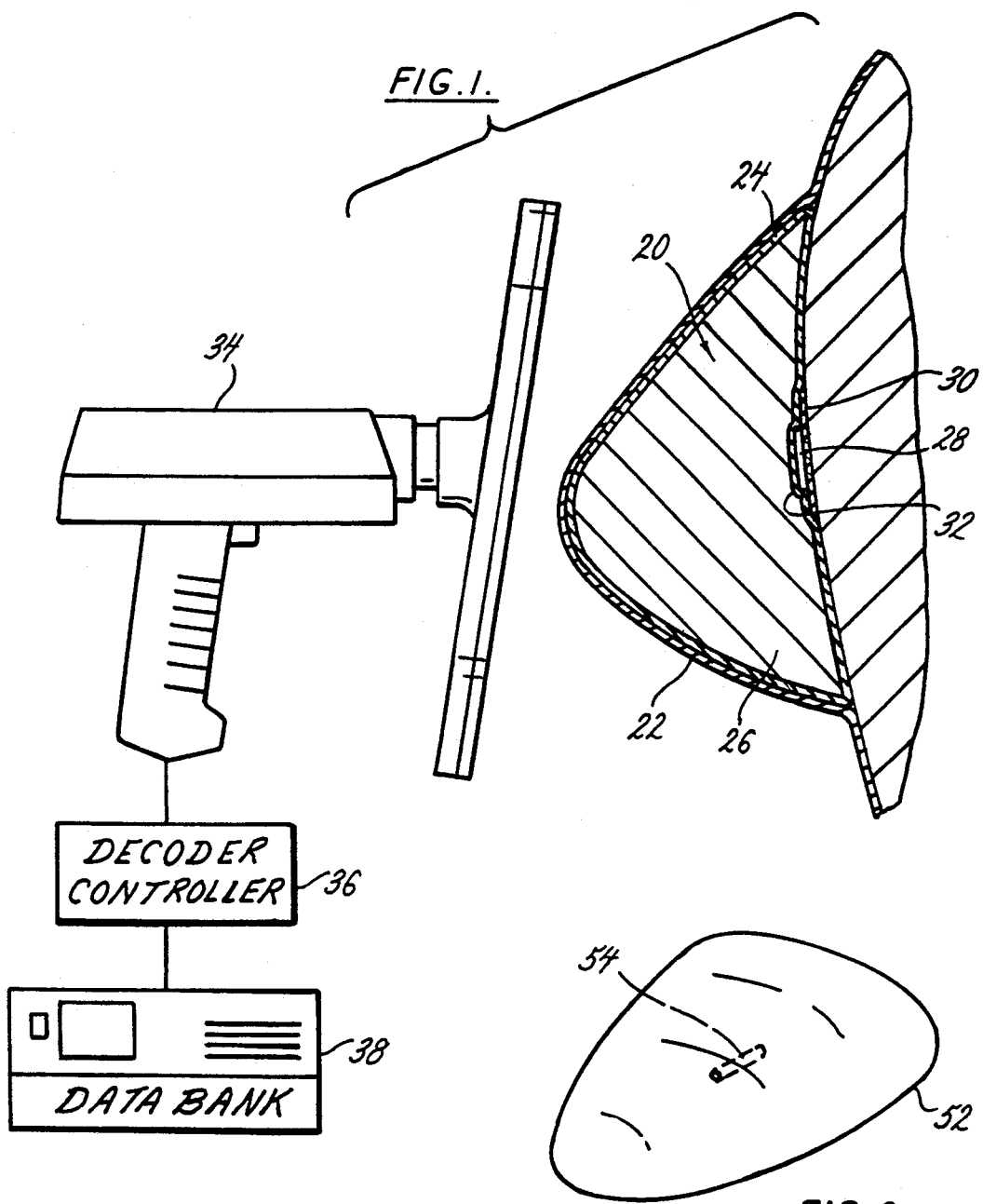
FIG. 1.
FIG. 3.
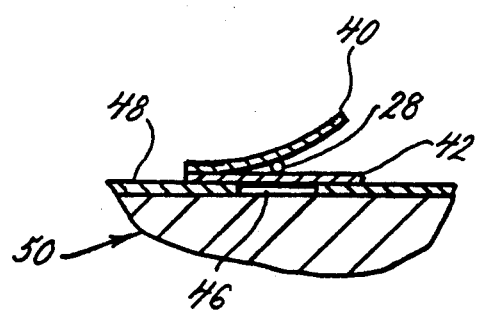
FIG. 2.

IMPLANT WITH ELECTRICAL TRANSPONDER MARKER

BACKGROUND AND SUMMARY OF THE INVENTION

With the advance of medical technology, there are a number of medical prostheses and devices which are implantable in humans for re-constructive and/or cosmetic purposes. These include breast implants; penile implants; musculature and other soft tissue implants; pace makers; valves; artificial joints and limbs such as knees, shoulders, legs, fingers, etc.; pins; screws; plates; rods; nails and other braces and supports. In order to ensure the continued safety and health of patients receiving these implants, the Safe Medical Device Act of 1990 has been enacted which dictates that manufacturers of Class III implantable medical devices institute a device registry for tracking of their devices, notification of patients, and otherwise monitoring these implants after they have been placed in a patient. Compliance with this Act has been proposed through a method of tracking which requires the surgeon who implants the device to complete and return a form or card with patient demographic data and implant data to the manufacturer or to a third party registry service. This method requires careful accumulation of data by a surgeon or his staff as well as secure inventory control procedures in order to ensure that the data is properly associated with the correct implant. Additionally, there is a risk of loss of the data entirely resulting from misdirected or lost communications. Furthermore, access to this data can be impeded in the event of an emergency situation or other circumstances which interfere with a patient's ability to recall or report the proper information which medical personnel may then use to access the registry and data contained therein.

There have been some suggestions in the prior art of marking the implants themselves with, for example, a radiopaque marker or other marker which contains the information relating to the implant. Ideally, this data could then be viewable by X-ray or some other non-invasive manner. However, there are difficulties with these prior art approaches. First of all, a breast implant with a radiopaque marker would at least partially obscure or mask tissue which is desired to be viewed in order to detect artifacts relating to tumors or the like for diagnosing cancer. Obviously, this is highly undesirable as the incidence of breast cancer presents a significant risk to many females. Additionally, repeated exposure to X-ray is not generally considered healthful or desirable and represents at least an added inconvenience entailing some degree of expense to recall or access the implant data. Therefore, radiopaque markers have not been viewed as a suitable long-term solution to this problem.

In order to solve these and other problems in the prior art, and in order to provide a convenient, fool proof marker secured to the implant itself and yet readable in a non-invasive manner, the inventors herein have succeeded in designing and developing an implant which incorporates a passive transponder which may be encoded and subsequently accessed with a hand held electromagnetic reader in a quick and inexpensive procedure. The passive transponder may be secured to the implant by any convenient means. For example, in a breast implant, the multi-layered shell for the implant may be laminated around the transponder to thereby be permanently and securely fixed to the implant. The transponder may be laminated in the sidewall of the shell, or between layers which comprise the seal patch which is applied to the shell to seal the mandrel opening. Similarly, the transponder may be laminated onto the surface of most other implants in an unobtrusive location. In some other implants, the transponder may be inserted into a hole or inlay and sealed in place.

As passive transponders are commercially available in a cylindrical shape sized at 2 mm in diameter and 11 mm in length, the patient will not sense any discomfort or even the presence of the transponder. Also, the transponder may be encoded with any suitable encoding scheme. A commercially available transponder presently provides for the storage of up to 64 binary bits of data. This data capacity may accommodate the direct storage of much, if not all, of the information desired to be recorded and maintained in a device registry. Furthermore, the storage capacity of the transponder is expected to be increased as further development occurs over time. Alternately, a number, collection of numbers, combination of numbers and letters, or other indirect code may be stored which after reading may be used to access a data bank which itself contains the desired information. Of course, if information is directly stored in the implant, it becomes immediately available upon reading the transponder. This provides ready access to information in emergency situations. Alternately, with the widespread availability, accessibility, and use of computers over telecommunications networks including telephone lines, it is not generally considered to be unduly limiting to provide that the code read from the transponder be then used to access an appropriate data bank in order to obtain the patient demographics, manufacturer's name, date of manufacture, surgeon's name, date of implantation, A companion hand held electromagnetic reader is also commercially available which emits a low frequency magnetic field to activate the passive transponder and thereby cause it to transmit its encoded data to the reader. With this particular commercial device, no battery or other source of electrical power need be included in the passive transponder. This further reduces the size required for the transponder and renders it particularly suitable to this application.

While the principal advantages and features of the present invention have been described above, a more complete and thorough understanding of the invention may be attained by referring to the drawings and description of the preferred embodiment which follow.

BRIEF DESCRIPTION OF THE DRAWINGS

FIG. 1 is a perspective view of a breast implant containing a passive transponder with a hand held reader in position to read the encoded data contained therein;

FIG. 2 is a partial cross-sectional view of the transponder as laminated between the multiple layers of a seal patch for a breast implant;

FIG. 3 is a perspective view of a pectoralis muscle implant with a passive transponder mounted therein;

DETAILED DESCRIPTION OF THE PREFERRED EMBODIMENT

Figure 4:
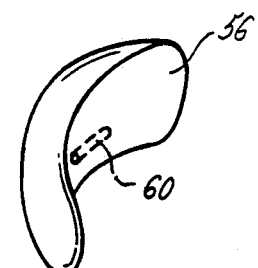
FIG. 4 is a perspective view of a soft chin implant with passive transponder mounted therein.

As shown in FIG. 1, a breast implant 20 has been implanted in a female's breast 22 and includes a silicone shell 24 inflated with an appropriate fill material 26. At the posterior side of the implant 20 is shown the transponder 28 which has been laminated between adjacent layers 30, 32 of the shell 24. Transponder 28 may be any passive transponder such as a Trovan Model ID100 available from Electronic Identification Systems Ltd. of Santa Barbara, Calif. This particular transponder is designed to be environmentally independent and suitable for operation while being directly submerged in liquids. Furthermore, it may be read spherically from any direction through most materials, and including most importantly those materials comprising implants for the human body. The transponder may be directly encoded with up to 64 binary bits of data to provide almost one trillion possible different code combinations. It is anticipated that FDA approval will be forthcoming for its use as part of the invention disclosed and claimed herein.

A hand held reader 34 is also shown in FIG. 1 and may be a Trovan Model LID500, or other suitable device. Its principle of operation includes emitting a low frequency magnetic field for activating the passive transponder 28. As such, transponder 28 has no power source and instead derives the energy needed for its operation from the magnetic field generated by the reader 34. This permits the transponder 28 to have a virtually unlimited life span. The hand held reader 34 is shown connected to a decoder controller 36 which accesses a data bank 38 in response to the detected code contained within transponder 28 to thereby access such data which has been stored corresponding to transponder 28. Alternately, as mentioned above, the hand held reader 34 may be used to access the code contained within transponder 28 and then other means used to access a data bank for the retrieval of the desired information. Such means might include the use of a telephone and modem to access a registry contained in a geographically centrally located site.

As shown in FIG. 2, the transponder 28 may be laminated between adjacent layers 40, 42 of the seal patch 44 which is commonly used to seal the mandrel opening 46 in a shell 48 of a breast implant 50. For other implants, convenient mounting locations may be readily determined with due consideration given to avoiding discomfort to the patient as well as optimizing readability of the transponder with the hand held reader.

As shown in FIG. 3, a pectoralis muscle implant 52 may conveniently have a passive transponder 54 contained therein. The passive transponder 54 may be molded in place, or a hole or inlay drilled for placement of the implant, after which the implant surface may then be refinished.

Figure 5:
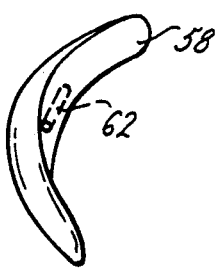
FIG. 5 is a perspective view of a rigid chin implant with a passive transponder mounted therein.
Figure 6:
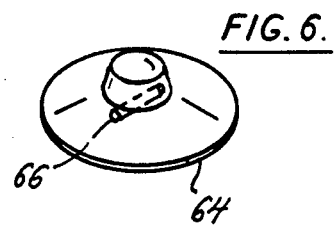
FIG. 6 is a perspective view of a nipple transplant with a passive transponder mounted therein.
Figure 7:
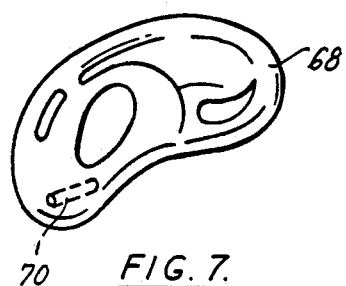
FIG. 7 is a perspective view of an otoplasty implant with a passive transponder mounted therein.
Figure 8:
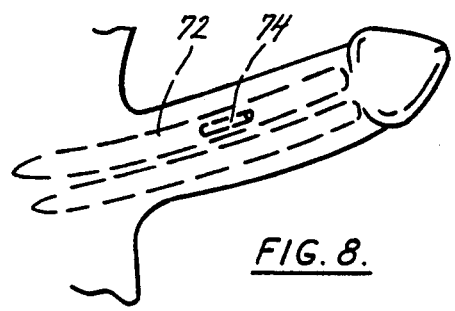
FIG. 8 is a perspective view of a penile implant, surgically implanted, with a passive transponder mounted therein.

As shown in FIGS. 4 and 5, a soft chin implant 56 or a hard chin implant 58 may also have a passive transponder 60, 62 mounted therein. As shown in FIG. 6, a nipple implant 64 has a passive transponder 66 mounted internally. In all of these transplants, the mounting of the passive transponder is achieved to provide minimal discomfort or sensation to the patient, as well as to avoid interference with the cosmetic appearance of the implant. As shown in FIG. 7, an otoplasty implant 68 may have a passive transponder 70 mounted therein. As shown in FIG. 8, a penile implant 72 may have a passive transponder 74 mounted therein.

Figure 9:
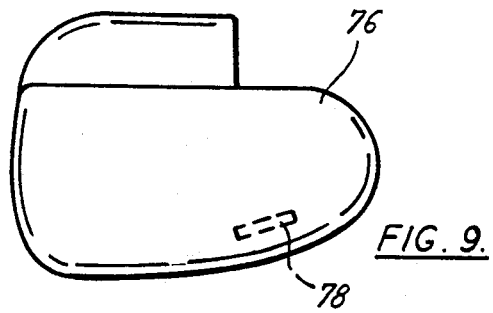
FIG. 9 is a top view of a pace maker with a passive transponder mounted thereon.
Figure 10:
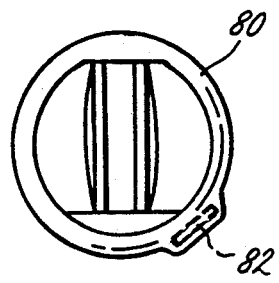
FIG. 10 is a top view of a heart valve with a passive transponder mounted to the edge thereof.

As shown in FIG. 9, a pace maker 76 may also have a passive transponder 78 mounted either on its surface or below the protective metal casing thereof. The inventors have found that reading of the passive transponder by the hand held reader may be achieved even when the transponder is obscured by metallic surfaces. As shown in FIG. 10, a heart valve 80 may have a passive transponder 82 mounted to its edge in order to avoid interference with the operability thereof, or fixation thereof.

Figure 11:
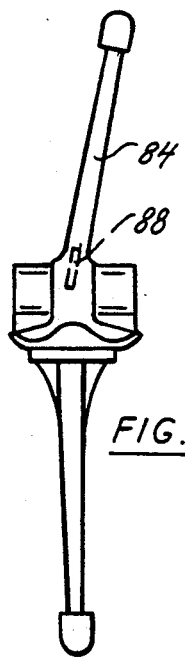
FIG. 11 is a perspective view of a total knee joint prosthesis with a passive transponder mounted thereon.
Figure 12:
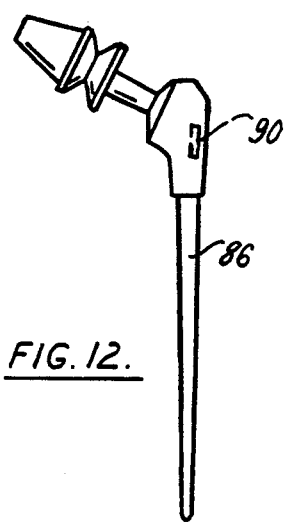
FIG. 12 is a perspective view of a shoulder arthroplasty system with a passive transponder mounted therein.

As shown in FIGS. 11 and 12, a total knee joint prosthesis 84 or a shoulder prosthesis 86, either one of which includes a majority of parts made from titanium or the like, may also conveniently carry a passive transponder 88, 90.

Figure 13:
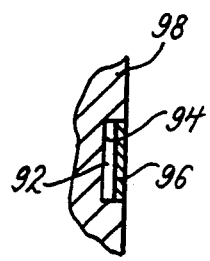
FIG. 13 is a partial cross-sectional view of a passive transponder inlaid into and below the surface of an implant.

As shown in FIG. 13, the passive transponder 92 may be placed within a trough 94 or the like and covered with a sealant 96 so that the surface of the transponder 98 is uninterrupted and smooth as is desirable in many transponders.

Figure 14:
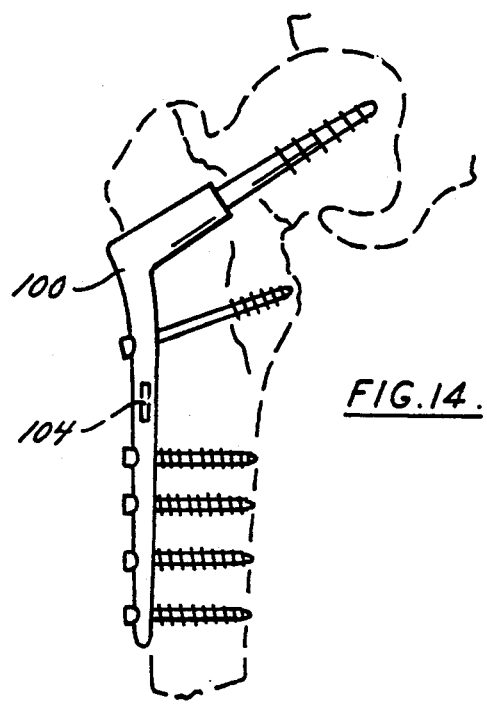
FIG. 14 is a perspective view of a femoral fixation system implanted in a femur with a passive transponder mounted thereto.
Figure 15:
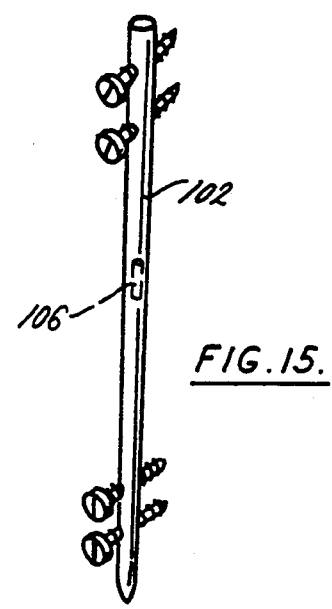
FIG. 15 is a perspective view of an orthopedic nailing system with a passive transponder mounted therein.
Figure 16:
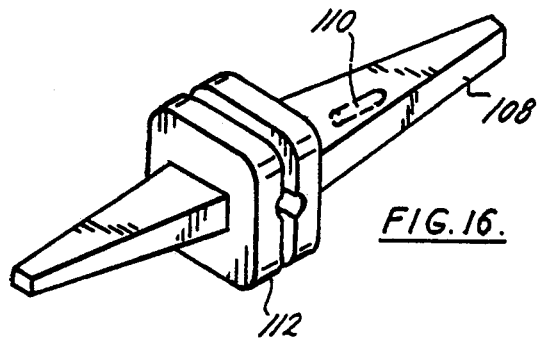
FIG. 16 is a perspective view of a finger joint prosthesis with a passive transponder mounted therein.
Figure 17:
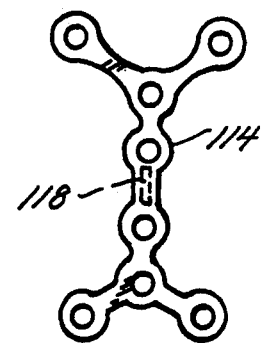
FIG. 17 is a perspective view of a craniomaxillofacial plating system with a passive transponder mounted therein.
Figure 18:
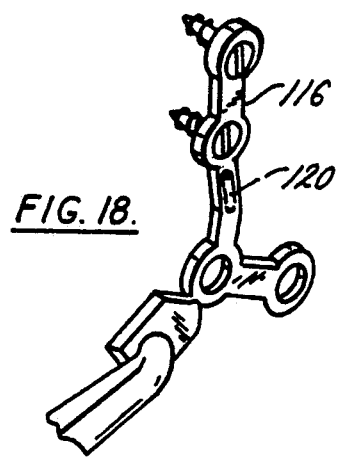
FIG. 18 is a perspective view of still another plating system with a passive transponder mounted therein.
Figure 19:
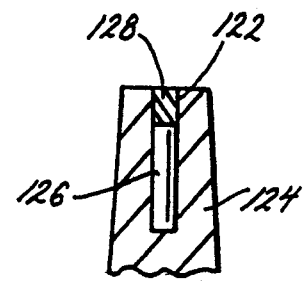
FIG. 19 is a partial cross-sectional view of a typical implant with a passive transponder mounted within a cored hole drilled therein.

As shown in FIGS. 14 and 15, a femoral fixation implant 100, or an orthopedic nailing system 102 may conveniently have a passive transponder 104, 106 inlaid therein. As shown in FIG. 16, a finger joint prosthesis 108 may also have a passive transponder 110 located in a position which does not interfere with the movable joint portion 112 of the prosthesis 108. As shown in FIGS. 17 and 18, a craniomaxillofacial plating system 114 or any other plating system 116 may also conveniently include a passive transponder 118, 120. As an alternative to the inlay mounting shown in FIG. 13, a hole 122 may be drilled in any convenient location of an implant 124 and the passive transponder 126 inserted therein and sealed in place by sealer 128, with the outer surface of sealer 128 being finished to provide a smooth surface on implant 124.

As disclosed herein, a wide variety of implants made of all sorts of material may conveniently include a passive transponder which may be implanted, and then read by the hand held reader. This compatibility and ease of operation permits the use of a passive transponder with virtually any implant. The inventors have disclosed herein a representative sample of such implants. However, the scope of the present invention is broad enough to encompass any implant presently known to the inventors herein.

There are various changes and modifications which may be made to the invention as would be apparent to those skilled in the art. However, these changes or modifications are included in the teaching of the disclosure, and it is intended that the invention be limited only by the scope of the claims appended hereto.

We claim:

1. In an implantable prosthesis adapted for implantation in a human, the improvement comprising a transponder mounted thereto so that said transponder is implanted as said prosthesis is implanted, said transponder having means for being encoded with a unique tag so that said transponder may be readily identified after implantation by reading said unique tag.

2. The prosthesis of claim 1 wherein said transponder has means for its tag to be read with a non-invasive protocol.

3. The prosthesis of claim 2 wherein said transponder has means for its tag to be read electromagnetically.

4. The prosthesis of claim 3 wherein said transponder has means for being energized by a remote reader thereby obviating a need for a battery to be contained in said transponder.

5. The prosthesis of claim 4 wherein said transponder has means for being encoded with a number selected from within a range of 0 to 64 bits, binary.

6. The prosthesis of claim 5 wherein said prosthesis is a breast implant including an envelope.

7. The prosthesis of claim 6 wherein said transponder is mounted to said implant by being laminated between layers of said envelope.

8. The prosthesis of claim 7 wherein said implant further comprises a seal patch on said envelope, said transponder being laminated into said seal patch.

9. The prosthesis of claim 1 wherein said transponder is mounted within a profile of said prosthesis.

10. The prosthesis of claim 9 wherein said transponder is sealed within a hole in said prosthesis.

11. The prosthesis of claim 1 wherein said prosthesis is a soft tissue implant.

12. The prosthesis of claim 1 wherein said prosthesis is a reconstructive bone implant.

13. The prosthesis of claim 1 wherein said prosthesis is a joint reconstructive implant.

14. The prosthesis of claim 13 wherein said prosthesis is a replacement joint.

15. A prosthesis intended for human implantation, said prosthesis including a transponder mounted thereto so that said transponder is implanted as said prosthesis is implanted, said transponder having means for being encoded with a unique identifier so that said transponder's identifier may be read after implantation and associated with a data base for reporting selected data corresponding to said implant.

16. The prosthesis of claim 15 wherein said transponder has means for its identifier to be read remotely.

17. The prosthesis of claim 16 wherein said transponder has means for its identifier to be read electromagnetically.

18. The prosthesis of claim 17 wherein said transponder has means for being energized by a remote reader thereby obviating a need for a battery to be contained in said transponder.

19. The prosthesis of claim 18 wherein said prosthesis is a breast implant comprised of an envelope with a multi-layered seal patch, said transponder being mounted therein by being sealed between the layers of said seal patch.

20. The prosthesis of claim 19 wherein said transponder has means for being encoded with a number selected from within a range of 0 to 64 bits, binary.

21. The prosthesis of claim 15 wherein said transponder is mounted within a profile of said prosthesis.

22. The prosthesis of claim 21 wherein said transponder is sealed within a hole in said prosthesis.

23. The prosthesis of claim 15 wherein said prosthesis is a soft tissue implant.

24. The prosthesis of claim 15 wherein said prosthesis is a reconstructive bone implant.

25. The prosthesis of claim 15 wherein said prosthesis is a joint reconstructive implant.

26. The prosthesis of claim 25 wherein said prosthesis is a replacement joint.

27. A breast implant comprised of an elastomeric shell, a multi-layered elastomeric seal patch adhered to said shell, and an electromagnetically readable transponder laminated between the layers of said seal patch, said transponder having means for being encoded with a unique code so that after implantation said code may be read by a remote, non-invasive reader to thereby learn selected data concerning said implant.

* * * * *